US00PP19788P2

(12) United States Plant Patent
Danziger

(10) Patent No.: US PP19,788 P2
(45) Date of Patent: Mar. 3, 2009

(54) ***SALVIA* PLANT NAMED 'DANSALFUN1'**

(50) Latin Name: *Salvia farinacea*
Varietal Denomination: DANSALFUN1

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,641

(22) Filed: Jan. 11, 2008

(51) Int. Cl.
*A01H 5/00* (2006.01)

(52) U.S. Cl. ..... Plt./475

(58) Field of Classification Search ..... Plt./263, Plt./475

See application file for complete search history.

*Primary Examiner*—Annette H Para
*Assistant Examiner*—S. B. McCormick Ewoldt

(57) ABSTRACT

A new and distinct *Salvia* cultivar named 'DANSALFUN1' is disclosed, characterized by having blue flowers, a compact, well-branched plant habit and early, continuous flowering. The new variety is a *Salvia,* normally produced as an outdoor garden or container plant.

2 Drawing Sheets

Latin name of the genus and species: *Salvia farinacea.*
Variety denomination: 'DANSALFUN1'.

BACKGROUND OF THE INVENTION

The new cultivar is a product of a planned breeding program, conducted by the inventor, Gabriel Danziger. The objective of the breeding program was to produce plants of *Salvia farinacea* with compact habits. The seed parent is the unpatented, proprietary seedling variety referred to as *Salvia farinacea* 'SAL 12.' The pollen parent is unknown as the new variety 'DANSALFUN1' is a result of open pollination, in which the pollen parent cannot be identified. The new variety was discovered on Aug. 6, 2005, by the inventor in a group of seedlings resulting from that crossing, in Moshav Mishmar Hashiva, Israel.

Asexual reproduction of the new cultivar 'DANSALFUN1' by vegetative cuttings was performed at a commercial greenhouse in Moshav Mishmar Hashiva, Israel and has shown that the unique features of this cultivar are stable and reproduced true to type on successive generations.

SUMMARY OF THE INVENTION

The cultivar 'DANSALFUN1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANSALFUNI' These characteristics in combination distinguish 'DANSALFUN1' as a new and distinct *Salvia* cultivar:

1. Compact plant habit.
2. Very well branched.
3. Grayed-Blue sepals.
4. Early, continuous flowering.

Plants of the new cultivar 'DANSALFUN1' are similar to plants of the parent, *Salvia farinacea* 'Sal 12' in most horticultural characteristics, however, plants of the new cultivar 'DANSALFUN1' are shorter, more compact and produce a more full plant with more lateral branches. The parent variety is the best commercial comparison to the new variety 'DANSALFUN1.'

BRIEF DESCRIPTION OF THE PHOTOGRAPH

Figure 1:
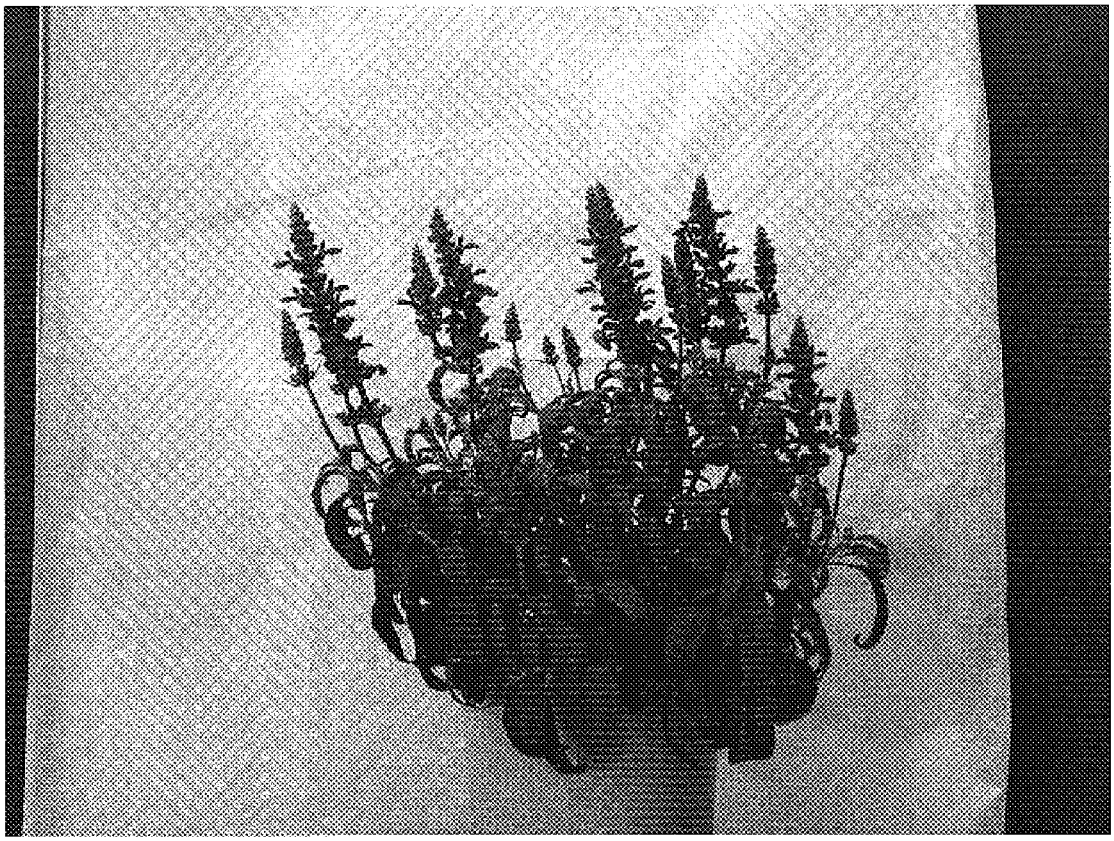
Figure 2:
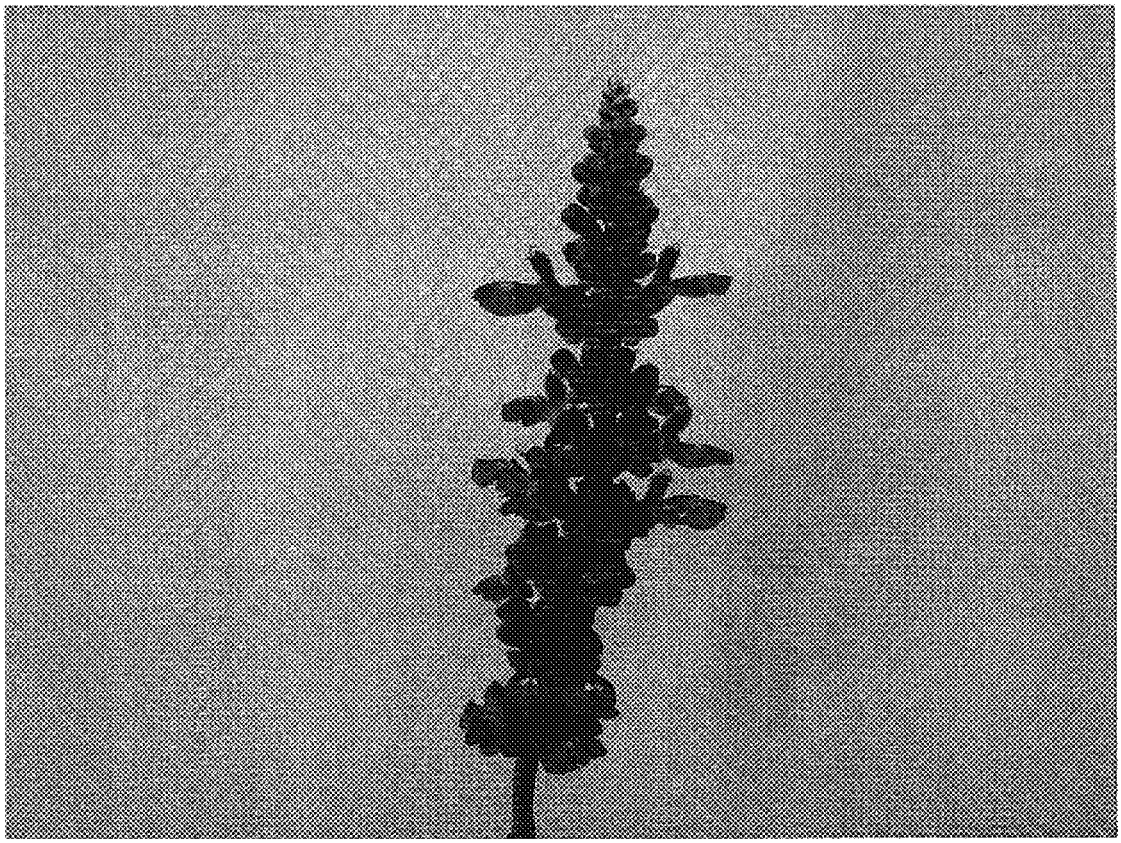

The accompanying photograph in FIG. 1 illustrates in full color a typical plant of 'DANSALFUN1' grown in a greenhouse, in a 12 cm pot. Age of the plant photographed is 6 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'DANSALFUN1' plants grown in a greenhouse in Moshav Mishmar Hashiva, Israel. The growing temperature ranged from 20° C. to 28° C. The greenhouse is un-shaded, giving bright, normal sunlight conditions. Measurements and numerical values represent averages of typical plant types.

Botanical classification: *Salvia farinacea* cultivar 'DANSALFUN1.'

PROPAGATION

Time to initiate roots: About 5–8 days at approximately 25° C.
Root description: Fine, densely fibrous.
Time to produce a rooted cutting: About 21 days at 25° C.

PLANT

Growth habit: Upright annual.
Pot size of plant described: 12 cm.
Height: Approximately 40 cm.

Plant spread: Approximately 30 cm.
Growth rate: Rapid.
Branching characteristics: Moderately free-branching, Approximately 2 primary branches with lateral branches forming potentially at every node.
Length of primary lateral branches: Approximately 15 cm.
Diameter of lateral branches: Approximately 0.8 cm.
Quantity of lateral branches: About 10.
Stem:
*Form.*—Square in cross-section.
*Color.*—Near RHS Green 143 C.
*Pubescence.*—Lightly pubescent with soft, short feather-like hairs.
Internode length: Approximately 0.3 cm.
Age of Plant Described: Approximately 6 weeks from a rooted cutting.

FOLIAGE

Leaf:
*Arrangement.*—Opposite.
*Quantity.*—Approximately 6 per main branch.
*Average length.*—Approximately 6.5 cm.
*Average width.*—Approximately 1.8 cm.
*Shape of blade.*—Lanceolate.
*Apex.*—Acute.
*Base.*—Attenuate.
*Attachment.*—Stalked.
*Margin.*—Slightly dentate.
*Texture of top surface.*—Matte.
*Pubescence.*—None.
*Color.*—Young foliage upper side: Near RHS Green 137B. Young foliage under side: Near RHS Green 137C. Mature foliage upper side: Near RHS Yellow-Green 146A. Mature foliage under side: Near RHS Yellow-Green 146B.
*Venation.*—Type: Pinnate. Venation color upper side: Near RHS Yellow-Green 146C. Venation color under side: Near RHS Yellow-Green 145C.
*Petiole.*—Average Length: Approximately 1.5 cm. Diameter: Approximately 0.1 cm. Color: Near Yellow-Green 146B.

FLOWER

Natural flowering season: Freely flowering under outdoors growing conditions with substantially continuous blooming from spring through autumn. Year round in greenhouse environment, or under warm conditions and high sunlight. Begins flowering between 6 to 9 weeks of planting a rooted cuttings.
Inflorescence type and habit: Flowers arranged in verticillasters on spikes.
Rate of flower opening: 3 days from bud to fully opened flower.
Flower Longevity on Plant: Individual flowers last 3 days on the plant. Each spike lasts approximately 5 weeks with flowers.
Quantity of flowers: About 4 buds and 8 fully opened flowers per lateral branch; about 10 blooming spikes per plant.
Inflorescence size:
*Diameter.*—Approximately 1.5 cm.
*Height.*—Approximately 15–18 cm.
Peduncle:
*Length.*—6–8 cm.
*Diameter.*—0.5 cm.
*Color.*—Near RHS Greyed-purple group N187C.
*Orientation.*—Upright, straight.
*Strength.*—Strong.

Corolla:
*Petal arrangement.*—The corolla is sympetalous and typically bilabiate with 2 lobes forming an upper lip and 3 lobes forming a lower lip
*Size.*—Small.
*Margin.*—Entire.
*Tip shape.*—Upper lip tip retuse, lower lip tip rounded.
*Length.*—Upper lip Approximately 0.3 cm, lower lip Approximately 0.7 cm.
*Texture.*—Upper lip Approximately 0.3 cm, lower lip Approximately 1 cm.
*Petal quantity.*—One upper lip and one lower lip with four lobes. Lips are fused at base.
*Petal apex shape.*—Obtuse.
*Texture.*—Upper lip has short, feather-like hairs, lower lip is smooth and hairless.
*Aspect.*—Acute angle to the stem.
*Petaloids.*—Upper lip has 2 petaloids, lower lip has 4 petaloids.
Color: Petals: When opening:
*Upper surface.*—Near RHS Violet-Blue 94A.
*Lower surface.*—Near RHS Violet-Blue 97C with 94B at the apex.
Fully opened:
*Upper surface.*—Near RHS Violet-Blue 94A.
*Lower surface.*—Near RHS Violet-Blue 97C with 94B at apex. At the middle of the lower surface, there is a blotch of Green-White 157D.
Bud.
*Shape.*—Ovoid.
*Length.*—Approximately 0.5 cm
*Diameter.*—Approximately 0.3 cm.
*Color.*—Upper Surface: Near RHS Violet-Blue 93A. Lower Surface: Near RHS Violet-Blue 93B.
Calyx:
*Arrangement.*—Acute angle to stem.
*Height.*—Approximately 0.5 cm.
*Diameter.*—Approximately 0.3 cm.
*Shape.*—Tubular.
Sepals:
*Shape.*—Quantity per flower: 2, fused to form a tube.
*Length.*—Approximately 0.5 cm.
*Width.*—Approximately 0.3 cm.
*Margin.*—Entire.
*Texture.*—Glabrous, surrounded with rough lines.
*Color.*—Immature: Near RHS White N155A, with Violet-Blue 92A at apex. Mature: Near RHS Violet-Blue 92D with Violet-Blue 93B at margin of apex.
Bracts:
*Quantity.*—2 at the base of each flower.
*Shape.*—Ovate.
*Tip.*—Aristate.
*Texture.*—Glabrous.
*Length.*—Approximately 1 cm.
*Width.*—Approximately 0.5 cm.
*Color.*—Upper surface: Near RHS Yellow-Green 145A. Lower surface: Near RHS Yellow-Green 145B.
Fragrance: Leaves have a moderate, sage-like odor.

REPRODUCTIVE ORGANS

Stamens:
*Number.*—2.
*Filament length.*—Approximately 0.5 cm.
Anthers:
*Shape.*—Very narrowly elliptic.
*Length.*—Approximately 2 mm.

*Color.*—Near RHS Grayed-Purple N186A.

*Pollen.*—Color: Near RHS Yellow-Orange 15A. Quantity: Not measured.

Pistil:

*Number.*—1.

*Length.*—Approximately 1 cm.

*Style.*—Length. Approximately 0.8 cm. Color: Almost all white Transparent with a touch of RHS Purple 76C along edge.

*Stigma.*—Shape: Two-parted, cleft. Color: Near RHS Purple N87B.

Ovary color: Near RHS Yellow-Green 150C.

OTHER CHARACTERISTICS

Seeds and fruits: 4 narrow, oval shaped seeds per flower.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'DANSALFUN1' as herein illustrated and described.

* * * * *